United States Patent
Early et al.

(10) Patent No.: US 11,083,445 B2
(45) Date of Patent: Aug. 10, 2021

(54) KNIFE AND RETRACTOR SYSTEM

(71) Applicants: John Early, Dallas, TX (US); Gregory Pomeroy, Gorham, ME (US); Adam Finley, Winona Lake, IN (US); Ryan Schlotterback, Fort Wayne, IN (US)

(72) Inventors: John Early, Dallas, TX (US); Gregory Pomeroy, Gorham, ME (US); Adam Finley, Winona Lake, IN (US); Ryan Schlotterback, Fort Wayne, IN (US)

(73) Assignee: Nextremity Solutions, Inc., Warsaw, IN (US)

( * ) Notice: Subject to any disclaimer, the term of this patent is extended or adjusted under 35 U.S.C. 154(b) by 0 days.

(21) Appl. No.: 15/476,333

(22) Filed: Mar. 31, 2017

(65) Prior Publication Data
US 2017/0281213 A1    Oct. 5, 2017

Related U.S. Application Data

(60) Provisional application No. 62/315,725, filed on Mar. 31, 2016.

(51) Int. Cl.
*A61B 17/32* (2006.01)
*A61B 17/02* (2006.01)
*A61B 17/3211* (2006.01)

(52) U.S. Cl.
CPC ...... *A61B 17/0218* (2013.01); *A61B 17/0206* (2013.01); *A61B 17/320016* (2013.01); *A61B 17/320036* (2013.01); *A61B 2017/320052* (2013.01); *A61B 2017/32113* (2013.01)

(58) Field of Classification Search
CPC ......... A61B 17/3209–3217; A61B 17/320016; A61B 17/320075; A61B 2017/32113
See application file for complete search history.

(56) References Cited

U.S. PATENT DOCUMENTS

| | | | | |
|---|---|---|---|---|
| 4,337,576 A | * | 7/1982 | Drost | A61B 17/3213 30/162 |
| 4,963,147 A | * | 10/1990 | Agee | A61B 17/320036 606/170 |
| 5,053,044 A | * | 10/1991 | Mueller | A61B 17/320725 604/96.01 |
| 5,403,337 A | * | 4/1995 | Platts | A61B 17/3213 30/151 |
| 5,776,156 A | * | 7/1998 | Shikhman | A61B 17/320016 606/167 |
| 5,968,061 A | | 10/1999 | Mirza | |

(Continued)

*Primary Examiner* — Eduardo C Robert
*Assistant Examiner* — Steven J Cotroneo
(74) *Attorney, Agent, or Firm* — Heslin Rothenberg Farley & Mesiti P.C.; Victor A. Cardona, Esq.

(57) ABSTRACT

A gastrocnemius knife and retractor system and kit includes a surgical knife and a soft tissue retractor. The soft tissue retractor is configurable to move from a collapsed mode to an expanded mode and back again, and can be inserted through a small incision when in the collapsed mode. Once inside the incision, the soft tissue retractor is expanded to permit visualization and accessibility of the surgery site. The surgical knife is then introduced and guided along a path in the frame of the soft tissue retractor, thereby incising the desired tissue. Once the tissue is incised, the surgical knife is withdrawn, followed by the soft tissue retractor after it is collapsed.

12 Claims, 11 Drawing Sheets

(56) References Cited

U.S. PATENT DOCUMENTS

| | | | |
|---|---|---|---|
| 6,383,188 B2* | 5/2002 | Kuslich | A61B 17/1617 408/158 |
| 6,923,813 B2* | 8/2005 | Phillips | A61B 17/1604 606/192 |
| 7,041,115 B2 | 5/2006 | Mirza et al. | |
| 8,911,470 B2 | 12/2014 | Mirza et al. | |
| 8,951,273 B1* | 2/2015 | Fard | A61B 17/320036 606/170 |
| 8,979,880 B2 | 3/2015 | Mirza et al. | |
| 9,066,746 B2 | 6/2015 | Mirza et al. | |
| 9,179,930 B2 | 11/2015 | Mirza et al. | |
| 9,211,136 B1 | 12/2015 | Mirza et al. | |
| 9,408,623 B2 | 8/2016 | Mirza et al. | |
| 9,445,830 B2 | 9/2016 | Mirza et al. | |
| 9,795,395 B2* | 10/2017 | Lizardi | A61B 17/1622 |
| 10,499,942 B2* | 12/2019 | Lown | A61B 17/320036 |
| 2005/0096645 A1* | 5/2005 | Wellman | A61B 17/320016 606/41 |
| 2007/0123889 A1* | 5/2007 | Malandain | A61B 17/1617 606/79 |
| 2007/0225740 A1* | 9/2007 | Suddaby | A61B 17/3211 606/170 |
| 2008/0195128 A1* | 8/2008 | Orbay | A61B 1/00052 606/170 |
| 2011/0144678 A1* | 6/2011 | Slater | A61B 17/3201 606/170 |
| 2012/0209274 A1* | 8/2012 | Belaney | A61B 17/1617 606/84 |
| 2013/0245638 A1* | 9/2013 | Horton | A61B 17/42 606/119 |
| 2014/0066963 A1 | 3/2014 | Mirza et al. | |
| 2016/0317177 A1 | 11/2016 | Mirza et al. | |
| 2016/0353973 A1 | 12/2016 | Mirza et al. | |
| 2016/0354103 A1 | 12/2016 | Mirza et al. | |
| 2017/0056047 A1* | 3/2017 | Keller | A61B 17/320016 |

\* cited by examiner

KNIFE AND RETRACTOR SYSTEM

CROSS REFERENCE TO RELATED APPLICATIONS

This application perfects and claims the benefit of U.S. Provisional Patent Application No. 62/315,725, filed on Mar. 31, 2016, and entitled Gastrocnemius Knife and Retractor System, which is hereby expressly incorporated herein by reference in its entirety.

BACKGROUND

The present disclosure relates to surgical instruments, and, more particularly, to a surgical knife and soft tissue retraction system to incise soft tissues.

In the field of surgery, there are medical conditions which necessitate operative intervention. One such condition is the inability to fully flex, or bend upwards a patient's foot. A surgical procedure used to address such a condition is the complete or partial release of the gastrocnemius tendon. This procedure is known as a Strayer Procedure, gastroc release, gastroc slide, tenotomy, or other terms. The cut tendon then heals in an elongated position, which allows more flexibility in the foot.

In a normal anatomy, the gastrocnemius and soleus muscles abut one another. It is necessary, then, to perform the incision on the gastrocnemius muscle without damaging the soleus muscle. In addition, visibility is limited as to the incision site and accordingly with regard to the target soft tissues that the user wants to avoid.

Although partial or complete release of the gastrocnemius tendon is discussed herein as an example, the inventions may also be used for other medical conditions such as plantar fasciitis or carpal tunnel syndrome.

Previous ways to alleviate these problems have been addressed in various ways. For example, surgical instruments attached to endoscopes can be inserted in and among the soft tissues in order to separate them and incise them. Alternatively, handheld retractors can be used by the surgeon and/or assistant in order to retract soft tissues to provide visualization of the incision site.

Another way to address the problem is a "low technology" solution: the surgeon simply creates an incision in the patient, digitally (with fingers) palpates and separates the soft tissues, and introduces a scalpel into the wound to incise the tendon.

What is needed in the art is a combination of a soft tissue retractor and a surgical knife which, through a minimally-invasive incision, allows a surgeon to visualize and reproducibly incise the target soft tissues in a safe and controlled manner.

SUMMARY

The present disclosure is directed to an improved surgical knife that has a controlled cutting depth and can provide illumination to the surgical site.

The present disclosure also provides an improved soft tissue retractor that is of a low profile when collapsed for introduction through a minimally-invasive incision, and expands to both retract soft tissues as well as provide a defined cutting path.

The present disclosure also provides a method of using the inventive surgical knife and inventive soft tissue retractor in a manner which provides the safe and reproducible incision of soft tissues in a procedure that is not "blind" to the surgeon.

An advantage of the present disclosure is that the operative area is directly illuminated by the surgical knife and/or soft tissue retractor, thereby eliminating the need for an external lighting source.

Another advantage of the present disclosure is that, as a result of the design of the surgical knife blade with relationship to the soft tissues retractor, the depth of the incision is controlled and limited to a predetermined depth.

Yet another advantage of the present disclosure is that the instruments may be disposable, thereby saving the cost and other detrimental aspects of sterilization and re-use.

Still another advantage of the present disclosure is the small profile of the soft tissue retractor allows it to be used in a minimally-invasive procedure.

Yet another advantage of the present disclosure is the surgical knife and soft tissue retractor can be made available in a sterilized, pre-packaged kit.

In one aspect, the present disclosure provides a surgical knife including a handle portion, a beam portion extending from the handle portion, and a nose portion defining a free end. The nose portion includes at least one blade support portion and a cutting blade coupled to the blade support portion. The cutting blade includes a working depth determined by the depth of a portion of the blade that protrudes past a bottom surface of the blade support in a cutting state.

In some embodiments, the working depth of the blade is adjustable. In some such embodiments, the working depth of the blade is adjustable within the range of 2 mm to 4 mm. In some embodiments, the knife further includes an adjustment knob configured to vary the depth of the portion of the blade that protrudes past the bottom surface of the blade support. In some embodiments, the cutting blade is retractable into a retracted state such that the blade does not protrude past the bottom surface of the blade support.

In some embodiments, the cutting blade includes a convex cutting edge. In some embodiments, the blade support portion includes at least one blade support extension that defines the bottom surface. In some such embodiments, the at least one blade support extension defines a planar outer surface. In some other such embodiments, the blade support portion includes a pair of blade support extensions that define a cavity therebetween, and wherein a portion of the blade is positioned within the cavity. In some such embodiments, the cutting blade includes a cutting edge, and at least a distal end of the cutting edge is positioned within the cavity.

In some embodiments, the knife further includes an illumination mechanism that provides illumination. In some embodiments, a handle portion defines an outer dimension that is larger than an outer dimension defined by the beam portion, and the knife further includes a transition portion extending between the handle portion and the beam portion.

In another aspect, the present disclosure provides a soft tissue retractor including a handle portion, a pivoting mechanism including a pivot bar attached to the handle, and a frame with first and second retractor plates. The at least one of the first and second retractor plates includes a knife slot. The first retractor plate is pivotably coupled to a first portion of the pivot bar and the second retractor plate is pivotably coupled to a second portion of the pivot bar such that rotation of the handle in a first direction translates the first and second retractor plates toward each other and rotation of the handle in a second direction that opposes the first direction translates the first and second retractor plates away from each other.

In some embodiments, the first and second retractor plates are translatable between a collapsed state with the first and second retractor plates abutting, and an expanded state with the first and second retractor plates spaced apart at a predefined distance. In some embodiments, the pivot bar is attached to the handle at a pivot point, the first retractor plate is pivotably coupled to the pivot bar at or on a first side of the pivot point, and the second retractor plate is pivotably coupled to the pivot bar on a second side of the pivot point.

In some embodiments, the retractor further includes at least one hinge member extending between and pivotably coupled to the first and second retractor plates. In some embodiments, the retractor further includes an end plate member extending between and pivotably coupled to the first and second retractor plates. In some embodiments, the first retractor plate is pivotably coupled to the first portion of the pivot bar via a first frame post, the second retractor plate is pivotably coupled to the second first portion of the pivot bar via a second first frame post, and an inner surface of at least one of the first and second pivot bars includes a convex engagement surface aligned with a knife slot thereof.

In another aspect, the present disclosure provides method including providing a kit including a surgical knife and a soft tissue retractor. The surgical knife includes a handle portion, a beam portion extending from the handle portion, and a nose portion defining a free end and including at least one blade support portion and a cutting blade coupled to the blade support portion. The cutting blade has a working depth determined by the depth of a portion of the blade that protrudes past a bottom surface of the blade support in a cutting state. The soft tissue retractor includes a frame with first and second retractor plates. At least one of the first and second retractor plates includes a knife slot. The first and second retractor plates are pivotably coupled to each other such that they are translatable toward each other into a collapsed state and translatable away from each other into an expanded state.

In some embodiments, the method further includes creating an incision in the skin to access a desired soft tissue structure, inserting the frame of the soft tissue retractor into the incision while in a collapsed state, expanding the frame of the soft tissue retractor into an expanded state, introducing the nose of the surgical knife into the knife slot of one of the first and second retractor plates such that the cutting blade extends past an outer surface of the respective first and/or second retractor plate, and advancing the surgical knife along the knife slot to cut the desired soft tissue structure at the outer surface of the respective first and or second retractor plate.

BRIEF DESCRIPTION OF THE DRAWINGS

The above-mentioned and other features and advantages of this disclosure will become more apparent and the disclosure will be better understood by reference to the following descriptions of embodiments of the disclosure taken in conjunction with the accompanying drawings, wherein.

Corresponding reference characters indicate corresponding parts throughout the several views. The exemplification set out herein illustrates embodiments of the disclosure, in one form, and such exemplification is not to be construed as limiting the scope of the invention in any manner.

DETAILED DESCRIPTION

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Any examples of parameters are not exclusive of other parameters of the disclosed embodiments. Components, aspects, features, configurations, arrangements, uses and the like described, illustrated or otherwise disclosed herein with respect to any particular embodiment may similarly be applied to any other embodiment disclosed herein.

The terms "proximal" and "distal" are used principally throughout this specification for convenience; but it is to be understood that these terms are not intended to be limiting. Thus "proximal" in this specification refers to the feature of the apparatus closest to the operator during use, and "distal" refers to the end of the apparatus farthest from the operator during use.

Referring now to FIGS. 1-4, there is shown an embodiment of a knife 10 according to the present disclosure. In some embodiments, the knife 10 may be a surgical knife that is particularly advantageous for cutting tissue or other anatomy. In some embodiments, the knife 10 may be configured to be particularly advantageous as a surgical knife for cutting at least a portion of a gastrocnemius tendon, for example, such as for a gastroc release surgery.

Figure 1:
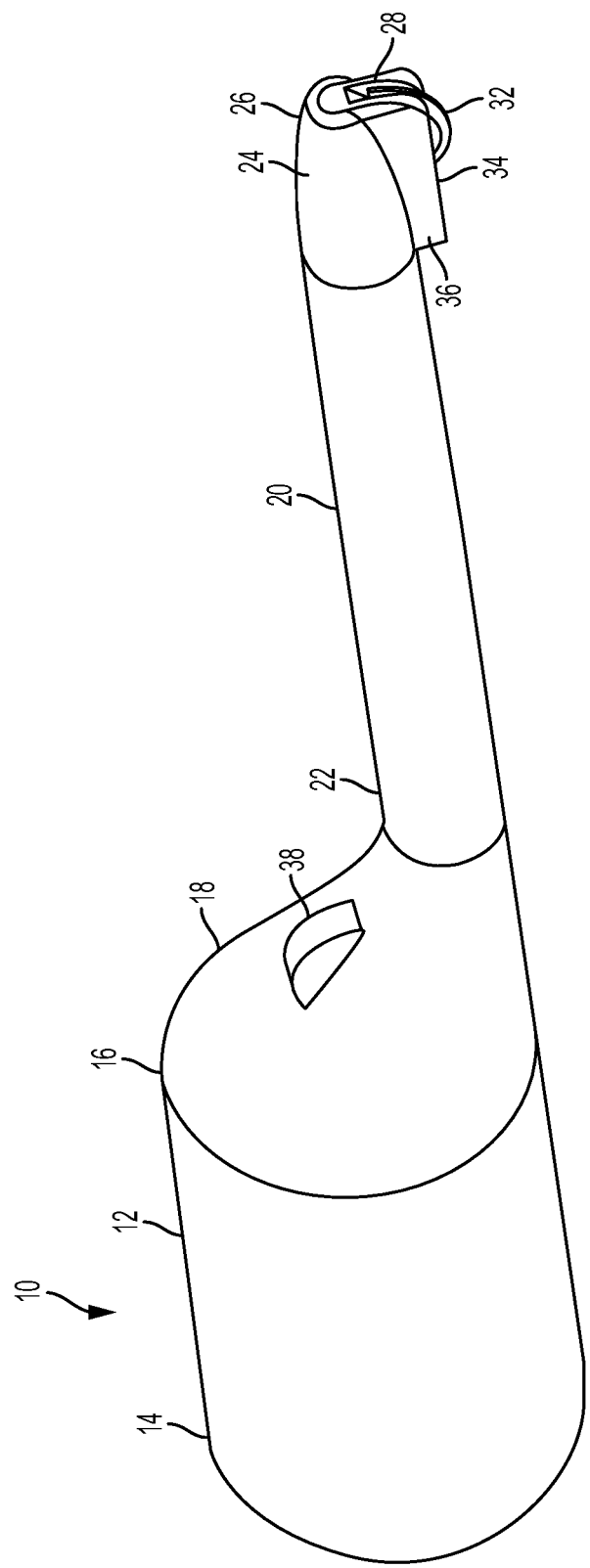
FIG. 1 is a perspective view of a surgical knife of the present disclosure.

In some embodiments, the knife 10 includes a handle 12, a beam 20, and a blade 32. The handle 12 of the knife 10 may include a proximal end 14 and a distal end 16, as shown in FIG. 1. In some embodiments, the handle 12 may include a cylindrical or substantially cylindrical cross-section. Alternatively, other cross-sectional geometries are possible, including any geometry that is functional and/or provides an ergonomic grip. The handle 12 may have a surface texture that provides a secure grip for the operator. In some embodiments, the handle 12 may also include batteries or other components, as discussed further below.

The beam 20 of the knife 10 may include a proximal end 22 and a distal end 24, as shown in FIG. 1. In some embodiments, the beam 20 may include, for example a cylindrical cross-section, as shown in FIG. 1. Alternatively, any other cross-sectional geometries may be utilized. The beam 20 may include batteries or other components, as further discussed below.

As shown in FIG. 1, the knife 10 may include a transition portion 18 disposed between the handle 12 and the beam 20. The transition portion 18 may be attached to the distal end 16 of the handle 12, and the proximal end 22 of beam 20. The attachment between the transition portion 18 and the other portions of the knife 10 may be permanent or modular; that is, the handle 12, the transition portion 18 and the beam 20 may be of one-piece construction or monolithic, or alternatively, the handle 12, the transition portion 18 and the beam 20 may be separate and distinct, or discrete, components that are attached to another component. The cross-sectional geometry of transition portion 18 may be any geometry that provides for a transition from the handle 12 to the beam 20. In some embodiments, the transition portion 18 may also include an adjustment knob 38 (discussed below) or other mechanical and/or electrical components.

The handle 12, the transition portion 18, and/or the beam 20 may be constructed from metal, plastic, polymer, or any other materials suitable for use in a surgical instrument. They may all be constructed from the same material, or they may be constructed from different materials.

Figure 2:
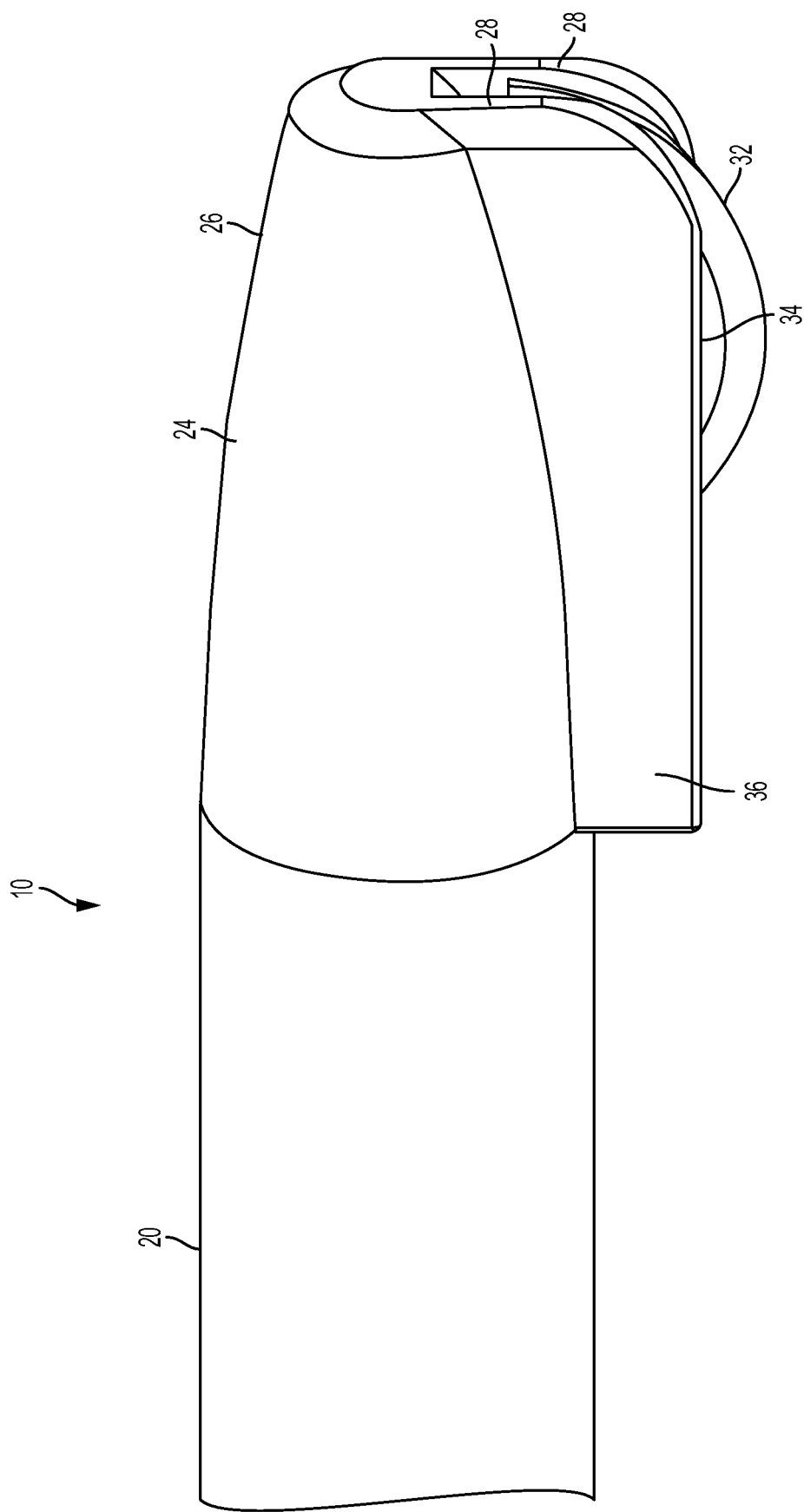
FIG. 2 is a perspective enlarged view of the distal end of the surgical knife of FIG. 1.

The distal end 24 of the beam 20 may include a nose 26, as shown in FIGS. 1 and 2. The nose 26 may include at least one blade support 28, which itself may include at least one blade support portion or extension 36 defining a blade support bottom 34, as shown in FIGS. 1 and 2. The nose 26 and its accompanying components may be of a geometry that allows it to function with a soft tissue retractor, as shown in FIGS. 5-10 and described below, and may include dovetails or other features to accomplish that function.

Figure 4:
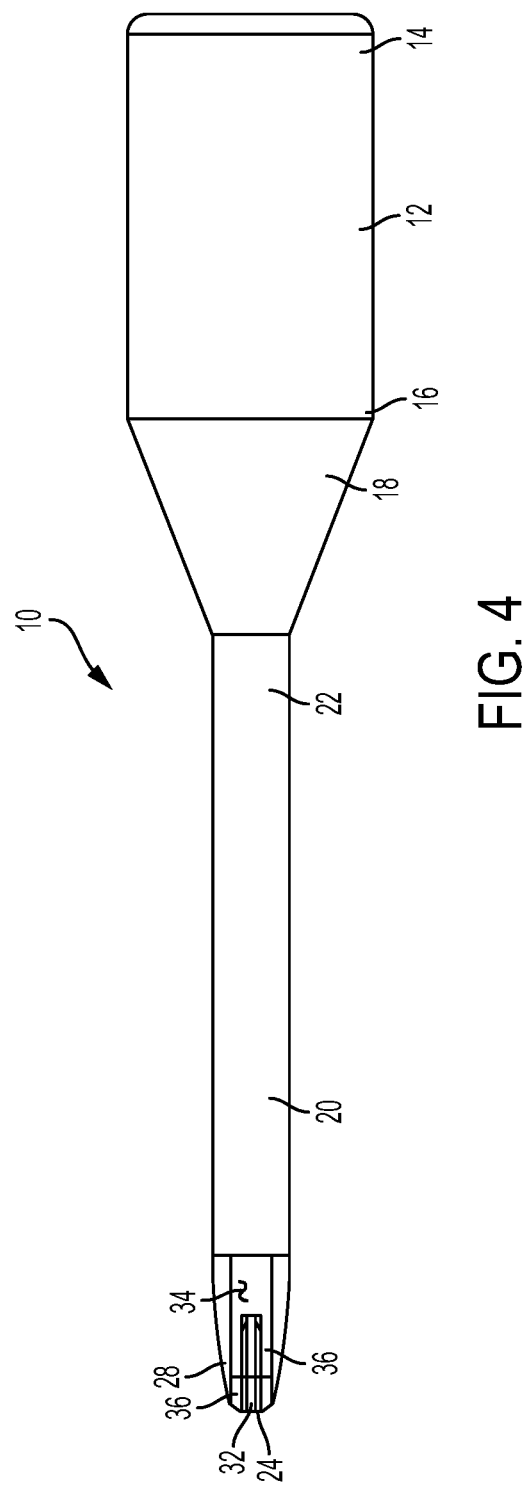
FIG. 4 is a bottom view of the surgical knife of FIG. 1.

The knife 10 may further include at least one blade 32, as shown in FIGS. 1, 2 and 4. In some embodiments, the blade 32 may be located or positioned in the nose 26 of the beam 20. The blade 32 may be of a half-circle geometry with a convex cutting edge to be used in a bi-directional manner. However, the blade 32 may be of any other geometry including circular, flat, pointed, or any other configuration that provides a cutting edge.

As shown in FIGS. 1, 2 and 4, the blade 32 may be held in place by a connection to or through the nose 26. For example, the blade 32 may be held by at least one blade support 28 as shown in FIGS. 1, 2 and 4 or through any other mechanism which is coupled to or extends from the beam 20, the transition portion 18, and/or the handle 12.

Figure 3:
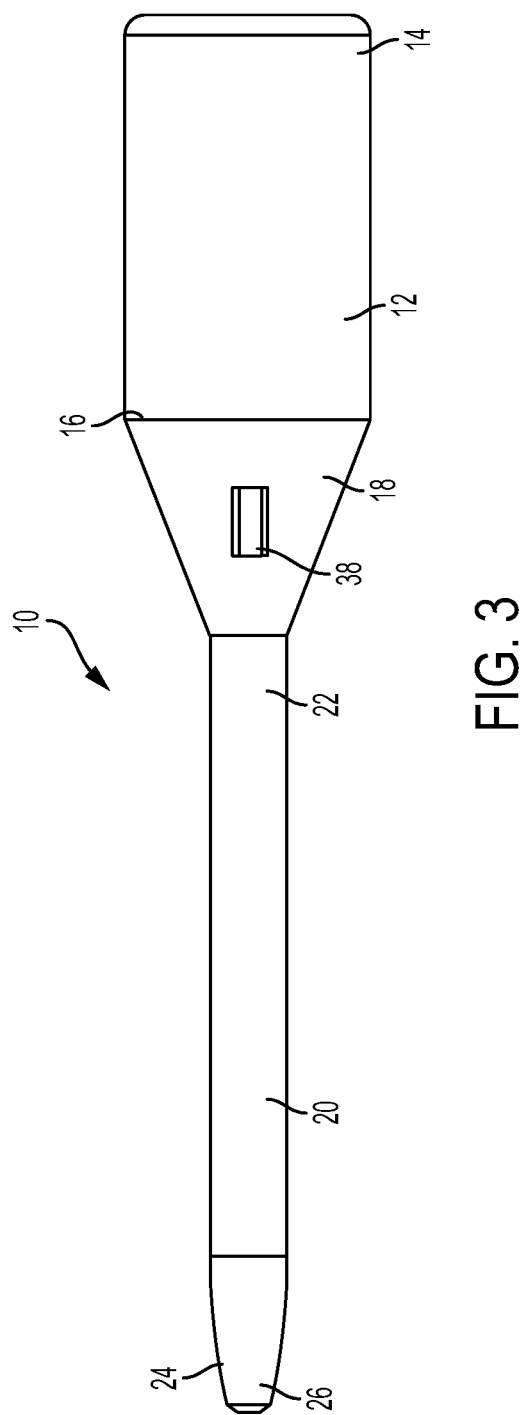
FIG. 3 is a top view of the surgical knife of FIG. 1.

The blade 32 may protrude or be exposed at a predetermined depth. In some embodiments, the amount or depth of the exposed portion of the blade 32 may be determined by its protrusion or extension past the blade support bottom or edge 34 of the blade support 28, as shown in FIGS. 1, 2 and 4. In this way, the depth of an incision may be determined by the blade 32 cannot go deeper than the amount of the exposed portion, such as the portion of the blade 32 that extends or protrudes beyond the blade support bottom 34. In some embodiments, the knife 10 may include a manually engageable adjustment knob 38 (e.g., positioned on or in the handle 12) that is configured to selectively set the depth of the blade 32, as shown in FIGS. 1 and 3. For example, the adjustment knob 38 may be configured to selectively adjust the amount or depth of the blade 32 that is exposed and/or to retract the blade 32 completely hidden, such that no portion of the blade 32 is exposed (e.g., position the blade 32 completely above the blade support bottom 34). The adjustment knob 38 may be configured to effectuate movement of the blade 32 with respect to the blade support bottom 34 and/or movement of the blade support 28 with respect to the blade 32.

When fully retracted (i.e., no portion of the blade 32 is exposed), inadvertent cutting may be prevented or avoided. In some embodiments, the blade 32 may be capable of being exposed (e.g., via the adjustment knob 38) to a depth or length of within the range of 2 mm to 4 mm for a cutting operation. In some embodiments, the blade 32 may exposed (e.g., via the adjustment knob 38) to a depth or length of 2 mm for a cutting operation. As shown in FIG. 2, in some embodiments the blade 32 may not extend past the free end of the distal end 24 of the beam 20, and/or may only be exposed below the bottom surface 34 of the blade support 28 (e.g., the bottom surface 34 of the at least one blade support extension 36). The blade support extension 36 may define an outer surface.

In some embodiments, the knife 10 may be configured to provide illumination and/or visualization of the surgical site, such as via at least one of a camera, CMOS, LED, bulb. In some embodiments, such an illumination and/or visualization mechanism may be positioned within the nose 26 of the knife 10. In some embodiments, to disperse light and/or ensure light reaches a surgical or cutting site, at least a portion of the knife 10 may be made of transparent materials. The illumination and/or visualization mechanism may be powered by one or more batteries or other electrical-power providing mechanism contained within the knife, such as within the handle 12 or any other portion of the knife 10. In this way, an external power source to power the illumination and/or visualization mechanism may be avoided or not needed. The at least one electrical-power providing mechanism may be pre-installed within the knife 10 such that it already installed when the knife 10 is supplied, or the electrical-power providing mechanism may be attached to the knife after it has been supplied. Alternatively, in some embodiments the knife 10 may be configured to operate (e.g., the illumination and/or visualization mechanism may be configured to operate) via at least one external power source that can be electrically coupled to the knife 10 prior to use. In some such embodiments, the knife 10 may include the external power source.

In some embodiments, the knife 10 may be configured to be disposed of after use (e.g., a cutting process). In some other embodiments, the knife 10 may be configured to be cleaned and/or sanitized and reused (e.g., in a subsequent cutting process).

Referring now to FIGS. 5-8, in some embodiments the knife 10 of the present disclosure (or another knife) may be configured to cooperate with a retractor 50. In some embodiments, the retractor 50 may be configured as a tissue retractor, such as a soft tissue retractor. The retractor 50 may include a handle 52, a frame 54, and a pivoting mechanism 56, as shown in FIGS. 5-8. The retractor 50 may be manufactured from metal, plastic, polymer, or any other materials suitable for use as a surgical instrument and capable of separating tissue. All components or portions of the retractor 50 may be constructed from the same material, or they may be constructed from different materials. The retractor 50 may be disposable after a single use, or may be configured to be cleanable (e.g., sterilizable), and thus reusable.

Figure 5:
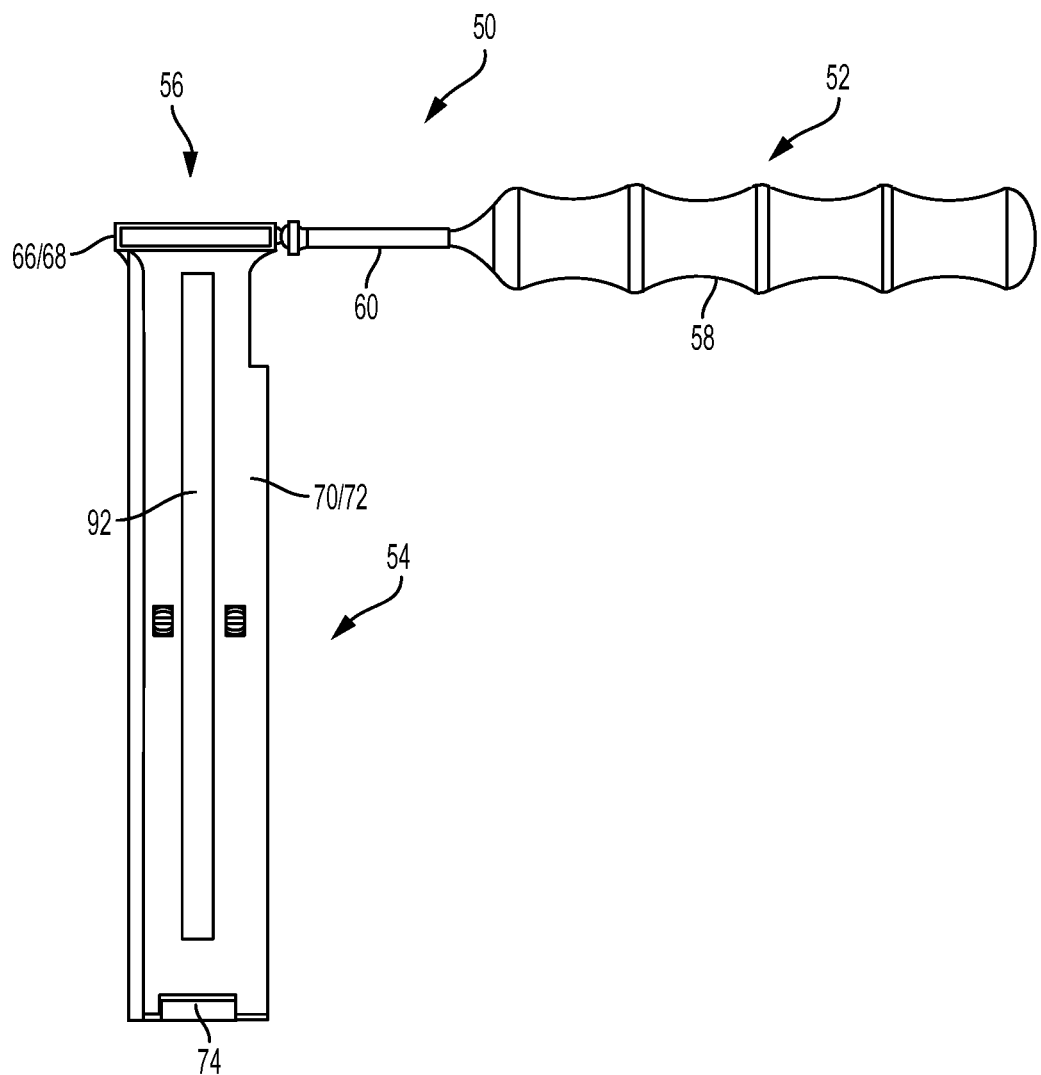
FIG. 5 is a top view of a soft tissue retractor of the present disclosure.

In some embodiments, the handle 52 of the retractor 50 may include a grip 58 and a shaft 60, as shown in FIG. 5. The handle 52 may be made of any material and any geometry which is ergonomic and capable of being held and manipulated by a user, such as a surgeon. The shaft 60 of the handle 52 may be fixedly attached to the grip 58, or may be removably attached to the grip 58 (e.g., via threads or any other mechanism). The location/position and/or orientation of the handle 52 in relation to other parts of the retractor 50 may be varied depending on the clinical situation and surgical exposure.

Figure 6:
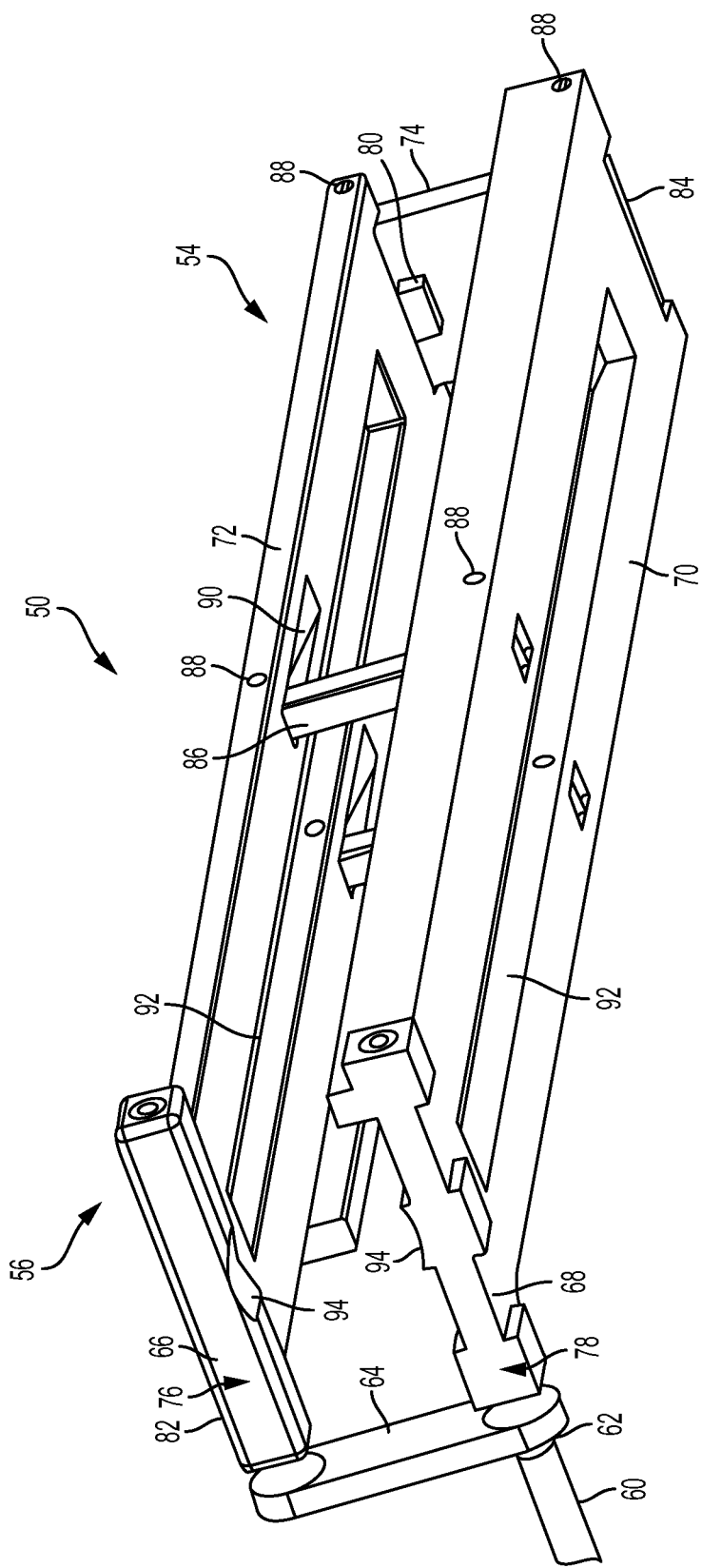
FIG. 6 is a perspective view of the frame and pivoting mechanism of the soft tissue retractor of FIG. 5.

With reference to FIG. 6, the frame 54 of the retractor 50 may include a proximal end 82 and a distal end 84. The retractor 50 may include frame posts 66, 68 at the proximal end 82 of the frame 54. The frame posts 66, 68 may each include an inner concave and/or radiused engagement surface 94 which facilitates the tracking and movement of the knife 10. The frame 54 of the retractor 50 may include an end plate 74 at the distal end 84 of the frame 54.

In further reference to FIG. 6, the frame 54 of the retractor 50 may include retractor plates 70, 72 extending at least partially between the frame posts 66, 68 and the end plate 74. The end plate 74 may be movably coupled (e.g., rotatably coupled about axes) to the retractor plates 70, 72. For example, the end plate 74 may be rotatably coupled to the retractor plates 70, 72 at pivot points or axes 88. In some such embodiments, the pivot points or axes 88 of the end plate 74 and the retractor plates 70, 72 may be pins or similar structures.

In some embodiments, at least one of the retractor plates 70, 72 may include or form at least one knife rail or slot 92 that extends at least partially along a direction extending between the frame posts 66, 68 and the end plate 74. In some embodiments, the at least one knife rail or slot 92 of the retractor plates 70, 72 may be elongated along a direction extending between the frame posts 66, 68 and the end plate 74. The one knife rail or slot 92 may be aligned with the engagement surface 94 of the frame posts 66, 68.

In some embodiments, at least one hinge member 86 may extend between and be movably coupled (e.g., rotatably coupled about axes) to the retractor plates 70, 72. For example, the at least one hinge 86 may be rotatably coupled to the retractor plates 70, 72 at pivot points or axes 88. In some such embodiments, the pivot points or axes 88 of the at least one hinge 86 and the retractor plates 70, 72 may be pins or similar structures. At least one of the retractor plates 70, 72 may include at least one relief or groove 90 corresponding to the at least one hinge 86 so that the hinge 86 can freely rotate with at least one of the retractor plates 70, 72 and extend therein to allow the retractor plates 70, 72 to move closer to each other into a collapsed state of the frame 54, as shown in FIG. 7.

In one exemplary embodiment, the hinge 86 may be positioned about midway along the length of retractor plates 70, 72. The hinge 86 may be configured to aid in stability of the frame 54 construct and/or prevent the knife 10 from skiving (as explained further below).

As shown in FIG. 6, the pivoting mechanism 56 of the frame 54 may be attached to the shaft 60 at pivot point 62, and include a pivot bar 64 which extends between the pivot posts 66, 68 (and thereby the ends of the retractor plates 70, 72). The pivot bar 64 may include pivot posts 76, 78 extending therefrom that are rotatably coupled with the posts 66, 68.

Figure 7:
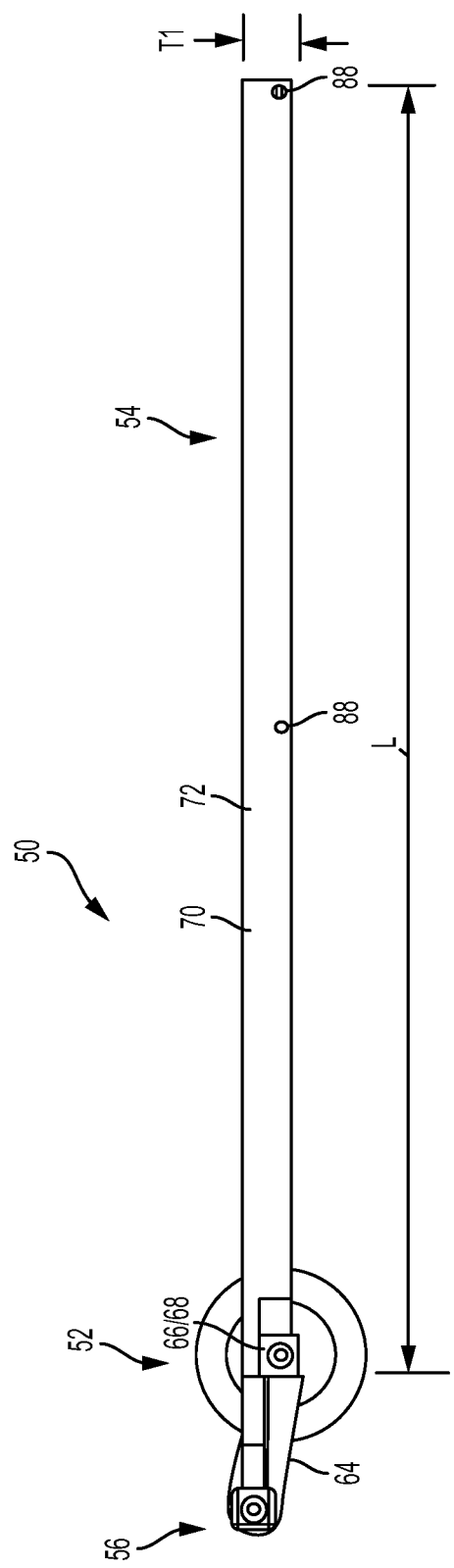
FIG. 7 is a side view of the soft tissue retractor of FIG. 5 in a collapsed mode.
Figure 8:
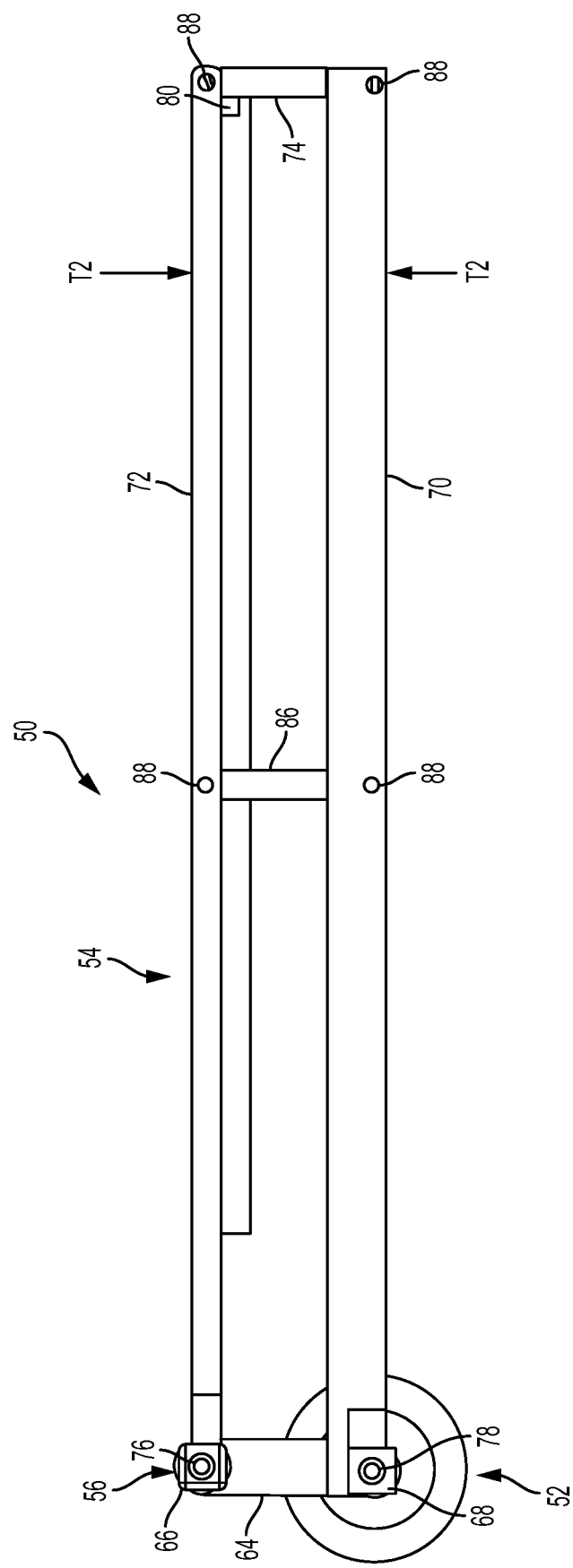
FIG. 8 is a side view of the soft tissue retractor of FIG. 5 in an expanded mode.

In use, the retractor 50 may initially be utilized in a fully or partially collapsed state of the frame 54 with the retractor plates 70, 72 being positioned substantially proximate to, or in abutment with, each other (i.e., minimal or no space between the retractor plates 70, 72), as shown in FIG. 7. The retractor 50, in the collapsed state (i.e., partially or fully collapsed), may be inserted through a skin incision and between two anatomical structures of interest (e.g., soft tissue of interest). After being positioned or insertion in a desired location between two anatomical structures of interest, the frame 54 of the retractor may be transitioned or activated into an expanded state such that the retractor plates 70, 72 are moved away from each other (i.e., space between the retractor plates 70, 72 is expanded), as shown in FIG. 8. The degree of spacing between the retractor plates 70, 72 in the expanded state may vary depending upon the particular anatomical structures of interest, for example.

Expansion of frame 54 from the collapsed state (see FIG. 7) to the expanded state (see FIG. 8) to may be accomplished by the twisting or rotating (e.g., manually) of the handle 58 (e.g., counterclockwise or clockwise) while the frame 54 is positioned between the tissues of interest. Rotation of the handle 58 may cause pivot bar 64, and thereby the attached (e.g., pivotally-attached) pivot posts 76, 78 to rotate about the axis of the shaft 60 and/or pivot point 62. In some embodiments, a first pivot post 78 may rotate coincidentally with the shaft 60, pivot point 62 and/or a first retractor plate 70, while a second pivot post 76 may rotate around the longitudinal axis of shaft 60 and/or pivot point 62, and thereby move in relation to the first pivot post 78.

The retractor plates 70, 72, by virtue of their pivotal or rotatable connection to the pivot posts 76, 78 by the frame posts 66, 68, are thereby forced apart or away from one another via the pivot bar 64 during rotation of the handle 58 in a rotational direction (and moved toward each other during rotation in an opposing direction), as shown in FIGS. 7 and 8. Movement of the retractor plates 70, 72 away from each other may also displace the anatomical structures of interest that the frame 54 is positioned between, away from each other.

As the end plate 74 and the at least one hinge 86 are pivotally or rotatably attached to the retractor plates 70, 72 via the pivot points 88, they are rotated or angled with respect to the retractor plates 70, 72 to an expansion position or orientation (see FIG. 8) from their previously collapsed position or orientation (see FIG. 7). The at least one relief 90 in the retractor plates 70, 72 associated with the at least one hinge 86 allows the at least one hinge 86 to fit therein so that the frame 54 can be completely collapsed such that the retractor plates 70, 72 abut to each other. The frame 54 may be configured to stop rotation of the at least one hinge 86, end plate 74 and/or pivot bar 64 with respect to the retractor plates 70, 72 from their collapsed orientation, and thereby movement of the retractor plates 70, 72 away from each other, at a particular point, such as when the retractor plates 70, 72 are spaced the maximum distance apart afforded by the at least one hinge 86, end plate 74 and/or pivot bar 64. For example, as shown in FIG. 6, rotation of the retractor plates 70, 72 may be stopped via at least one boss 80 (e.g., positioned on the end plate 74 or elsewhere) engaging with at least one of the retractor plates 70, 72 (such as at full expansion of the framed 54). When frame 54 is fully collapsed, the at least one boss 80 may be configured to fit within at least one knife rail or slot 92 or within a relief or other opening, for example.

In some embodiments, in a collapsed state, such as in the fully collapsed state with the retractor plates 70, 72 in abutment, the frame 54 may define a thickness T1 with a range of 2 mm to 3 mm, as shown in FIG. 7. In some embodiments, in an expanded state, such as in the fully expanded state with the retractor plates 70, 72 positioned furthest from each other as provided for by the frame 54, the frame 54 may define a thickness T2 with a range of 10 mm to 30 mm, such as about 20 mm, as shown in FIG. 8. The length L of the frame 54, such as the length L of the retractor plates 70, 72 and/or the between the end plate 74 and the frame posts 66, 68, may be within the range of 75 mm and 225 mm, as shown in FIG. 7. In one exemplary embodiment, a length L of the frame 54 may be 150 mm. The length of an incision in a patient adequate to allow the frame 54 to be positioned between two anatomical structures of interest, may be within the range of 15 mm to 50 mm, such as about 20 mm. However, in some other embodiments the retractor 50 may define other dimensions of the thickness in a collapsed state T1, the thickness in an expanded state T2 and/or the length L of the frame 54 outside of these ranges.

As noted above an illumination and/or visualization mechanism may be incorporated into retractor 50, such as into the frame 54, to assist in visualization during insertion, expansion and/or cutting via the knife 10. For example, a light may be emitted toward the surgical site upon opening the frame 54 to an expanded position.

Figure 9:
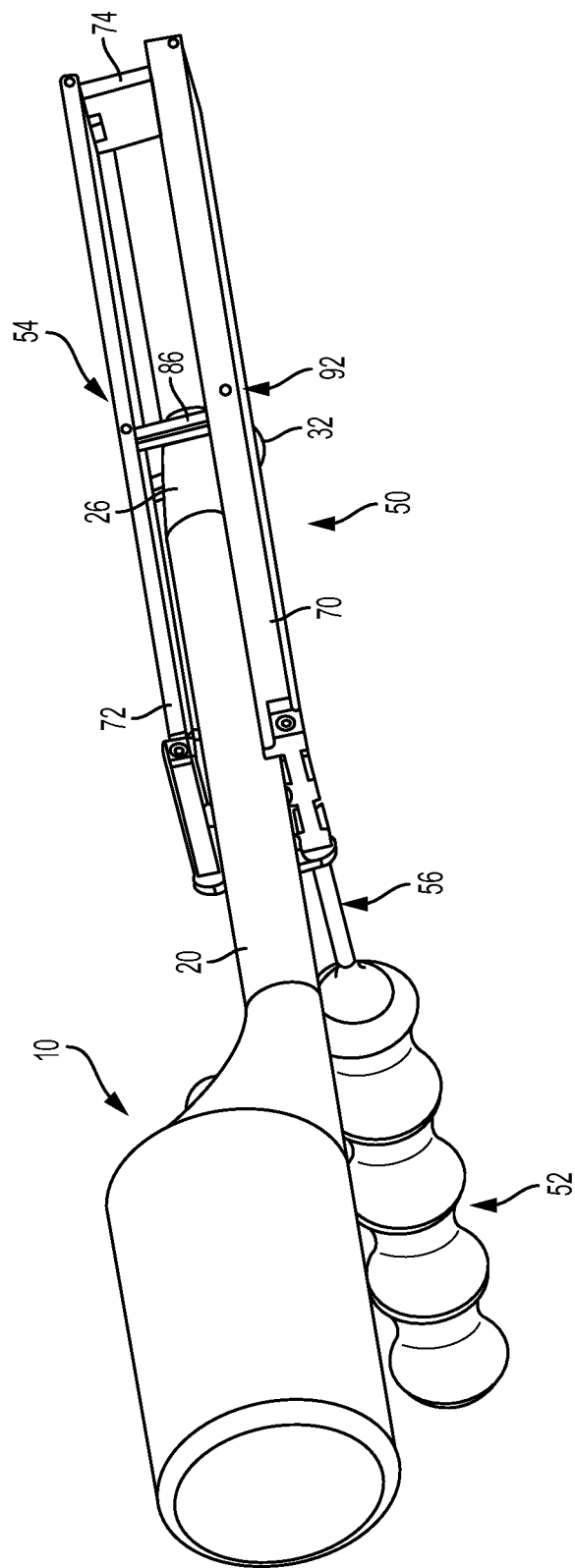
FIG. 9 is a perspective view of the surgical knife of FIG. 1 and the soft tissue retractor of FIG. 5 in an assembly of the present disclosure.
Figure 10:
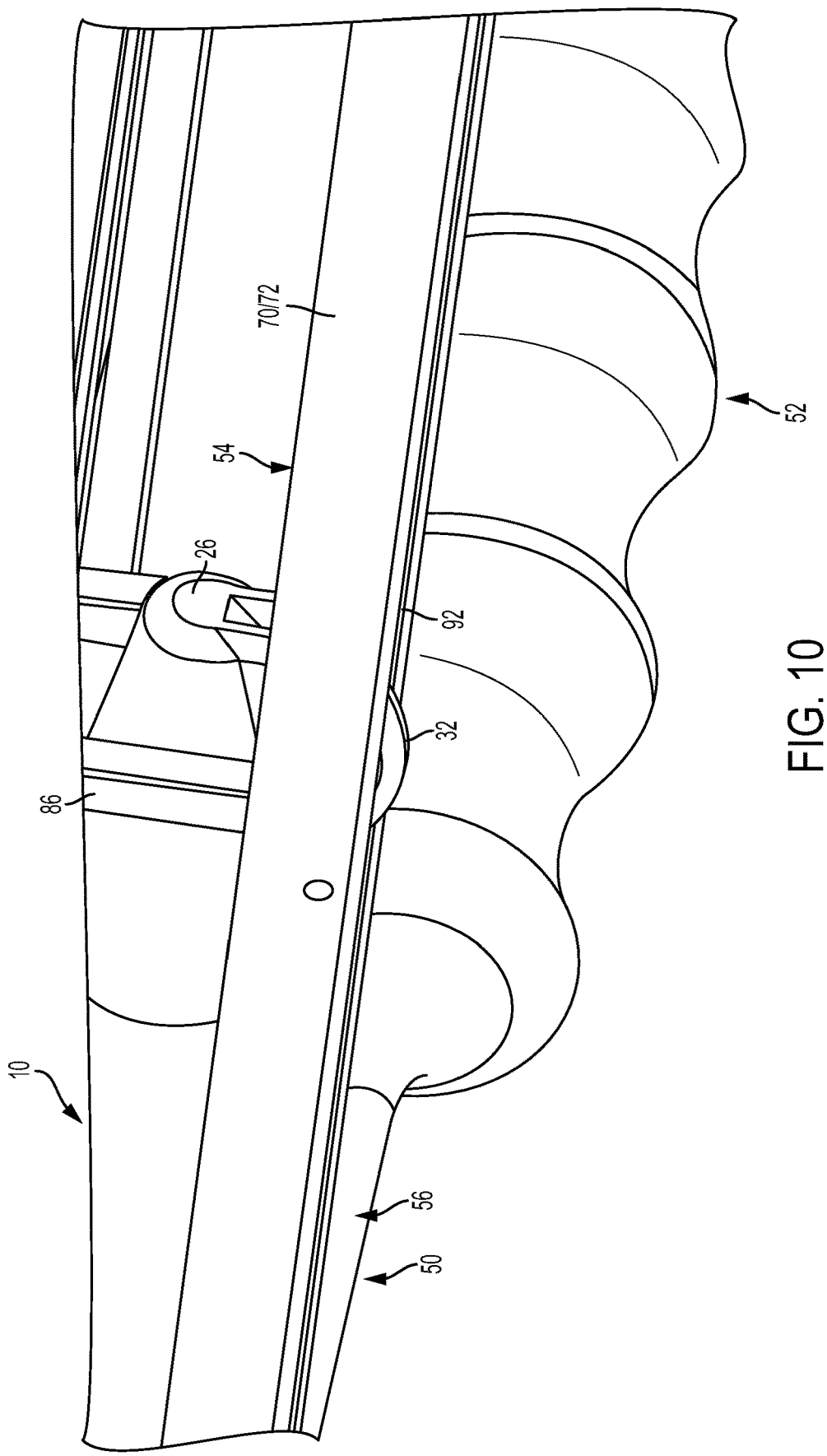
FIG. 10 is an enlarged perspective view of a portion of the assembly of FIG. 9.

Once the frame 54 has been inserted in vivo and moved into an opened state (i.e., the retractor plates 70, 72 are moved away from each other from the collapsed state or relative position), the surgical knife 10 may be introduced into frame 54, as shown in FIGS. 9 and 10. The knife 10 may be introduced into frame 54 by placing the blade 32 and a portion of the nose 26 (e.g., the at least one blade support 28 and/or at least one blade support extension side 36) of the knife 10 into at least one of the at least one knife rails or slots 92 of the retractor plate 70, 72. The blade 32 may extend past the bottom surface of the respective retractor plate 70, 72 of the knife rail or slot 92 that the blade 32 is positioned within, as shown in FIGS. 9 and 10. In this way, at least a portion of the exposed portion of the blade 32 of the knife 10 may extend beneath the frame 54. The knife 10 may also be introduced into frame 54 such that the engagement surfaces 94 contact and support the beam 20 of the knife 10, as shown in FIG. 9.

In some embodiments (not shown), the nose 26 of the knife 10 and/or at least one of the retractor plates 70, 72 may be configured to be integrated in some manner, rather than have the nose 26 of the knife 10 rest in the knife rail or slot 92 as described above. For example, the nose 26 and at least one of the retractor plates 70, 72 may include mating features that slidably or translatably couple these two structures together. The mating features may physically guide the nose 26 portion of the knife 10 tool along at least one of the retractor plates 70, 72 as the nose 26 portion moves along the respective knife rail or slot 92. For example, the retractor plates 70, 72 and/or the nose 26 portion may include a groove (e.g., a dovetail) and a projection that engages or is captured in the groove to physically guide the knife 10 as it translates along the respective knife rail or slot 92. As another example, the retractor plates 70, 72 and/or the nose 26 portion may include a captured sleeve to physically guide the knife 10 as it moves along the respective knife rail or slot 92.

Once the blade 32 and a portion of the nose 26 are positioned into at least one of the knife rails or slots 92 of the retractor plates 70, 72, the knife 10 may be manually advanced along the length of the at least one knife rail or slot 92 to simultaneously cut the desired tissue positioned at or against the bottom surface of the respective retractor plate 70, 72 of the knife rail or slot 92 that the blade 32 is positioned within. In some embodiments, the knife 10 may be used in the knife rail or slot 92 of only one of the retractor plates 70 or 72, and then removed and reintroduced along the knife rail or slot 92 of the other retractor plate 70, 72. Therefore, two incisions can be made while leaving the soft tissue retractor 50 in place within the patient.

The nose 26 and the blade 32 of the knife 10, and the at least one knife rail or slot 92 of the retractor 50, may be configured to complement each other such a portion of the knife 10 is captured by and continuously rides along the respective knife rails or slots 92 as is translated therethrough.

As described above, the protrusion of the knife blade 32 under the nose 26, as well as the thickness of the retractor plates 70, 72, allows the blade 32 to extend past the bottom or outer surface of the retractor plates 70, 72 and create an incision in the tissue of a predetermined depth (see FIGS. 9 and 10). In some embodiments, the at least one hinge 86 may prevent the knife 10 from skiving during a cutting procedure, and the engagement surface 94 of one or both of the retractor plates 70, 72 may support and guide the beam 20 of the knife 10 to ensure a continuous and stable operation as shown in FIG. 9. In some embodiments, the frame 54 may be configured such that in the opened state, such as the fully opened state, both the engagement surfaces 94 of the retractor plates 70, 72 support and guide the beam 20 of the knife 10 to ensure a continuous and stable operation as shown in FIG. 9.

After one or more incisions have been made in one or more soft tissue structures via the blade 32 of the knife 10, knife 10 may be withdrawn from the frame 54. The soft tissue retractor 50 may then be moved to a collapsed state, such as the fully collapse state, and withdrawn from the surgical site of the patient.

In some embodiments, that at least one knife 10 and at least one retractor 50 may be supplied as, or otherwise, form, a kit. In some embodiments, the at least one knife 10 and at least one retractor 50 may be supplied or provided in a sterilized state, either alone or within a case.

Figure 11A:
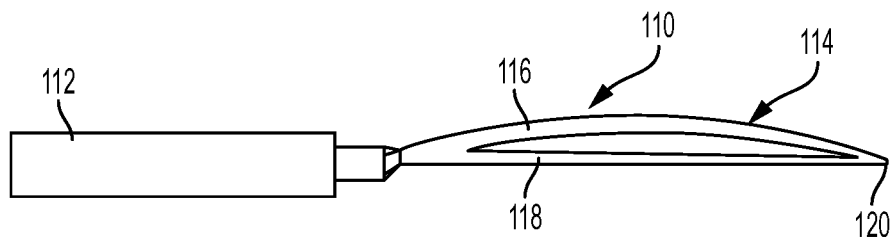
FIG. 11A is a side view of an expansion mechanism configured to expand the soft tissue retractor of FIG. 5.
Figure 11B:
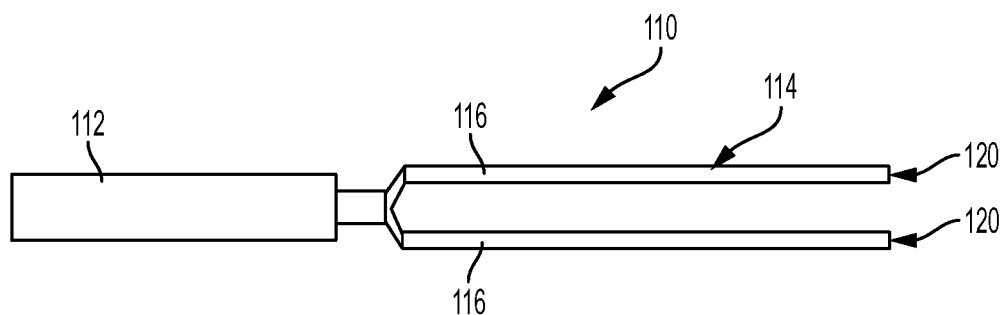
FIG. 11B is a top view of the expansion mechanism of FIG. 11A.
Figure 11C:
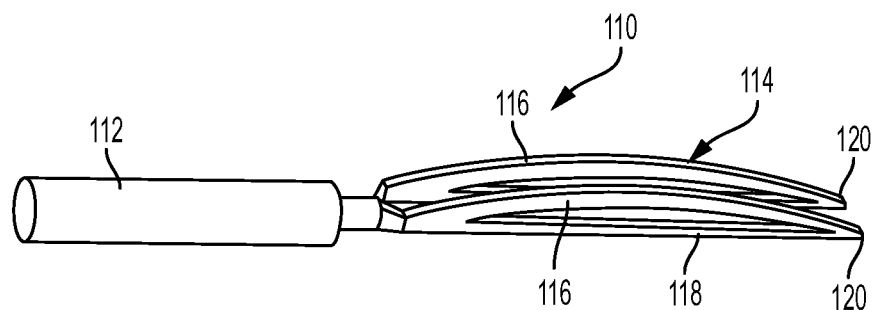
FIG. 11C is a perspective view of the expansion mechanism of FIG. 11A.

FIGS. 11A-11C illustrate an expansion mechanism 110 configured to manually expand the frame 54 of the retractor 50 from a collapsed state to an expanded state, as described above. Rather than including and/or utilizing the handle portion 52 and/or the pivoting mechanism 56 of the retractor 50, the expansion mechanism 110 may be utilized to move the retractor plates 70, 72 away from each other and into an expanded state. As shown in FIGS. 11A-11C, the expansion mechanism 110 may include a handle portion 112 and an expansion portion 114 extending from the handle portion 112. The expansion portion 114 of the expansion mechanism 110 may include at least tine 120 that defines a free end. As shown in FIGS. 11A-11C, in some embodiments, the expansion portion 114 of the expansion mechanism 110 may include a pair of tines 120 to that correspond to the retractor plates 70, 72.

As shown in FIGS. 11A-11C, the at least one tine 120 may include a lower engagement member 118 and an upper engagement member 116. The upper engagement member 116 may extend away from the lower engagement member 118, as shown in FIGS. 11A-11C. For example, the lower engagement member 118 may be substantially linear or flat, and the upper engagement member 116 may be angled, arcuate or otherwise shaped such that a portion of the upper engagement member 116 that is distal to the free end thereof is positioned further away from the lower engagement member 118 than at or proximate to the free end.

In use, the free end of the at least one tine 120 of the expansion portion 114 of the expansion mechanism 110 may be inserted into the frame 54 between the retractor plates 70, 72 of the retractor 50 when the retractor 50 is positioned between anatomical structures in a collapsed state, such as between soft tissue structures. The at least one tine 120 may be inserted such that the upper engagement member 116 engages an upper retractor plate 70 (or another portion of the retractor 50 coupled to the upper retractor plate 70 of the retractor 50) and the lower engagement member 118 engages a lower retractor plate 72 of the retractor 50 (or another portion of the retractor 50 coupled to the lower retractor plate 70). The at least one tine 120 may be inserted further inserted into the frame 54 of the retractor 50 such that the upper and lower engagement members 116, 118 moves or translates the upper and lower retractor plates 70, 72 away from each other and into an extended state, such as the fully extended state. The expansion mechanism 110 may then be removed from within the frame 54 of the retractor 50, or remain within the frame 54, when the knife 10 is inserted into the frame 54 to cut the tissue.

In some embodiments, the expansion mechanism 110 may be a separate and distinct component from the knife 10 and/or the retractor 50 assembly, and may or may not be supplied separately. In other embodiments, the expansion mechanism 110 may be movable coupled to the knife 10 and/or the retractor 50, and potentially supplied with the knife 10 and/or the retractor 50.

While knives and retractors and related methods have been described with respect to exemplary embodiments, the knives, retractors and related methods can be modified within the spirit and scope of this disclosure. This application is therefore intended to cover any variations, uses, or adaptations of the knives, retractors and related methods using its general principles. Further, this application is intended to cover such departures from the present disclosure as come within known or customary practice in the art to which this invention pertains and which fall within the limits of the appended claims. For example, it is to be understood that the above description is intended to be illustrative, and not restrictive. Numerous changes and modifications may be made herein by one of ordinary skill in the art without departing from the general spirit and scope of the invention as defined by the following claims and the equivalents thereof. For example, the above-described embodiments (and/or aspects thereof) may be used in combination with each other. In addition, many modifications may be made to adapt a situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description.

The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Also, the term "operably connected" is used herein to refer to both connections resulting from separate, distinct components being directly or indirectly coupled and components being integrally formed (i.e., monolithic). Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure. It is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the disclosure may include only some of the described embodiments. Accordingly, the inventions are not limited by the foregoing description, but is only limited by the scope of the appended claims.

This written description uses examples to disclose the invention, including the best mode, and to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A surgical knife, comprising:
a handle;
a beam extending from the handle; and
a nose connected to said beam and defining a free end opposite said handle, said nose including at least one blade support and a cutting blade held by the blade support, the cutting blade including a working depth determined by the depth of a portion of the blade that protrudes past a bottom surface of the blade support in a cutting state;
said handle comprising a handle bottommost surface and said beam comprising a beam bottommost surface, said handle bottommost surface and said beam bottommost surface aligned with each other in a direction parallel to longitudinal dimensions of said handle, said beam and said nose;
said blade support comprises a pair of blade support extensions defining a cavity therebetween, and said blade comprising a blade portion positioned within the cavity;
said blade support extensions extending downwardly relative to said handle bottommost surface and said beam bottommost surface, such that extension bottommost surfaces of said blade support extensions are located at a fixed depth in a direction transverse to the longitudinal dimension of said handle, said beam and said nose, and relative to said handle bottommost surface and said beam bottommost surface along entire longitudinal dimensions of said extension bottommost surfaces in the cutting state and in a non-cutting state, such that said blade support extensions extend away from a remainder of said nose, and said working depth is below said extension bottommost surfaces of said blade support extensions in the cutting state; and said blade support extensions extending from said free end of said nose toward said handle a distance past said blade in the cutting state and in the non-cutting state, such that said blade portion remains in said cavity between said blade support extensions for an entire dimension of said blade from said free end toward said handle in the cutting state and in the non-cutting state.

2. The surgical knife of claim 1, wherein the working depth of the blade is adjustable.

3. The surgical knife of claim 2, wherein the working depth of the blade is adjustable within the range of 2 mm to 4 mm.

4. The surgical knife of claim 2, further comprising an adjustment knob configured to vary the depth of the portion of the blade that protrudes past the bottom surface of the blade support portion.

5. The surgical knife of claim 2, wherein the cutting blade is movable into a retracted state such that the blade does not protrude past the bottommost surface of said blade support extensions.

6. The surgical knife of claim 1, wherein the cutting blade includes a convex cutting edge.

7. The surgical knife of claim 1, wherein the at least one blade support extension defines a planar outer surface.

8. The surgical knife of claim 1, wherein the handle extends past a top surface of said beam opposite said bottommost beam surface and in an opposite direction from said blade support extensions extending relative to said handle bottommost surface and said beam bottommost surface.

9. The surgical knife of claim 1, further comprising a light source to provide illumination.

10. The surgical knife of claim 1, wherein the handle portion defines an outer dimension that is larger than an outer dimension defined by the beam portion, and further comprising a transition portion extending between the handle portion and the beam portion.

11. The surgical knife of claim 1, wherein the cutting blade is movable from said non-cutting state into said cutting state such that the blade remains at a same longitudinal position relative to a longitudinal dimension of said nose.

12. A surgical knife, comprising:
a handle;
a beam extending from the handle; and
a nose connected to said beam and defining a free end opposite said handle, said nose including at least one blade support and a cutting blade held by the blade support, the cutting blade including a working depth determined by the depth of a portion of the blade that protrudes past a bottom surface of the blade support in a cutting state;

said handle comprising a handle bottommost surface and said beam comprising a beam bottommost surface, said handle bottommost surface and said beam bottommost surface aligned with each other in a direction parallel to longitudinal dimensions of said handle, said beam and said nose;

said blade support comprises a pair of blade support extensions defining a cavity therebetween, and said blade comprising a blade portion positioned within the cavity;

said blade support extensions extending downwardly relative to said handle bottommost surface and said beam bottommost surface, such that said blade support extensions extend away from a remainder of said nose, and said working depth is below extension bottommost surfaces of said blade support extensions in the cutting state; and said blade support extensions extending from said free end of said nose toward said handle a distance past said blade, such that said blade portion remains in said cavity between said blade support extensions for an entire dimension of said blade from said free end toward said handle, and said extension bottommost surfaces extending downwardly further than said handle bottommost surface and said beam bottommost surface, and being fixed relative to said handle bottommost surface and said beam bottommost surface along entire longitudinal dimensions of said extension bottommost surfaces in the cutting state and in the non-cutting state.

* * * * *